(12) United States Patent
Podmore et al.

(10) Patent No.: US 8,444,637 B2
(45) Date of Patent: May 21, 2013

(54) STEERABLE ABLATION DEVICE

(75) Inventors: Jonathan L. Podmore, San Carlos, CA (US); Gregory J. Kampa, Castaic, CA (US); Andrew Radin, Palo Alto, CA (US)

(73) Assignee: St. Jude Medical, Atrial Filbrillation Division, Inc., St. Paul, MN (US)

( * ) Notice: Subject to any disclaimer, the term of this patent is extended or adjusted under 35 U.S.C. 154(b) by 1274 days.

(21) Appl. No.: 11/647,315

(22) Filed: Dec. 29, 2006

(65) Prior Publication Data

US 2008/0161798 A1 Jul. 3, 2008

(51) Int. Cl.
*A61B 18/18* (2006.01)
*A61M 25/092* (2006.01)

(52) U.S. Cl.
USPC .......................................... 606/41; 604/95.04

(58) Field of Classification Search
USPC .......................................... 606/41; 604/94.05
See application file for complete search history.

(56) References Cited

U.S. PATENT DOCUMENTS

| | | | |
|---|---|---|---|
| 5,318,525 A | 6/1994 | West et al. | |
| 5,322,064 A * | 6/1994 | Lundquist | 600/381 |
| 5,368,564 A | 11/1994 | Savage | |
| 5,391,147 A | 2/1995 | Imran et al. | |
| 5,397,304 A | 3/1995 | Truckai | |
| 5,431,168 A | 7/1995 | Webster, Jr. | |
| 5,478,330 A | 12/1995 | Imran et al. | |
| 5,562,619 A * | 10/1996 | Mirarchi et al. | 604/95.04 |
| 5,588,964 A | 12/1996 | Imran et al. | |
| 5,611,777 A | 3/1997 | Bowden et al. | |
| 5,656,029 A | 8/1997 | Imran et al. | |
| 5,827,278 A | 10/1998 | Webster, Jr. | |
| 5,836,947 A | 11/1998 | Fleischman et al. | |
| 5,865,800 A | 2/1999 | Mirarchi et al. | |
| 5,871,525 A * | 2/1999 | Edwards et al. | 607/104 |
| 5,885,278 A | 3/1999 | Fleischman | |
| 5,897,529 A | 4/1999 | Ponzi | |
| 5,910,129 A | 6/1999 | Koblish et al. | |
| 5,916,213 A | 6/1999 | Haissaguerre et al. | |
| 5,935,124 A | 8/1999 | Klumb et al. | |
| 5,957,882 A * | 9/1999 | Nita et al. | 604/22 |
| 5,971,983 A | 10/1999 | Lesh | |
| 6,002,955 A | 12/1999 | Willems et al. | |
| 6,004,269 A | 12/1999 | Crowley et al. | |
| 6,023,638 A | 2/2000 | Swanson | |
| 6,024,740 A | 2/2000 | Lesh et al. | |
| 6,027,473 A | 2/2000 | Ponzi | |
| 6,048,329 A | 4/2000 | Thompson et al. | |
| 6,064,905 A | 5/2000 | Webster, Jr. et al. | |

(Continued)

OTHER PUBLICATIONS

International Search Report and Written Opinion of the International Searching Authority for PCT/US07/88633 dated Jun. 26, 2008.

*Primary Examiner* — Linda Dvorak
*Assistant Examiner* — Amanda Scott
(74) *Attorney, Agent, or Firm* — Wiley Rein LLP

(57) ABSTRACT

The invention relates to a flexible assembly for use in a region of a medical or surgical device. In preferred embodiments, the flexible region comprises a set of pull wires for controllably moving a treatment end of the device, and elements to separate the pull wires and maintain the integrity of the shaft of the flexible region in order to improve the operating aspects of the device. The devices and methods can be especially useful in ablation treatments, such as ablation at cardiac or epicardial tissues.

23 Claims, 6 Drawing Sheets

U.S. PATENT DOCUMENTS

| | | | |
|---|---|---|---|
| 6,066,125 A | 5/2000 | Webster, Jr. | |
| 6,068,629 A | 5/2000 | Haissaguerre et al. | |
| 6,071,274 A | 6/2000 | Thompson et al. | |
| 6,071,279 A | 6/2000 | Whayne et al. | |
| 6,071,282 A | 6/2000 | Fleischman | |
| 6,076,012 A | 6/2000 | Swanson et al. | |
| 6,080,151 A | 6/2000 | Swartz et al. | |
| 6,083,222 A | 7/2000 | Klein et al. | |
| 6,090,104 A | 7/2000 | Webster, Jr. | |
| 6,117,101 A | 9/2000 | Diederich et al. | |
| 6,120,476 A | 9/2000 | Fung et al. | |
| 6,123,699 A | 9/2000 | Webster, Jr. | |
| 6,164,283 A | 12/2000 | Lesh | |
| 6,171,277 B1 | 1/2001 | Ponzi | |
| 6,198,974 B1 | 3/2001 | Webster, Jr. | |
| 6,203,525 B1 | 3/2001 | Whayne et al. | |
| 6,210,362 B1 | 4/2001 | Ponzi | |
| 6,210,407 B1 | 4/2001 | Webster | |
| 6,212,426 B1 | 4/2001 | Swanson | |
| 6,214,002 B1 | 4/2001 | Fleischman | |
| 6,221,070 B1 | 4/2001 | Tu et al. | |
| 6,224,587 B1 * | 5/2001 | Gibson | 604/528 |
| 6,245,064 B1 | 6/2001 | Lesh et al. | |
| 6,254,599 B1 | 7/2001 | Lesh et al. | |
| 6,264,654 B1 | 7/2001 | Swartz et al. | |
| 6,270,496 B1 * | 8/2001 | Bowe et al. | 606/41 |
| 6,305,378 B1 | 10/2001 | Lesh | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,330,473 B1 | 12/2001 | Swanson et al. | |
| 6,371,955 B1 | 4/2002 | Fuimano et al. | |
| 6,383,151 B1 | 5/2002 | Diederich et al. | |
| 6,402,746 B1 | 6/2002 | Whayne et al. | |
| 6,416,511 B1 | 7/2002 | Lesh et al. | |
| 6,454,758 B1 | 9/2002 | Thompson et al. | |
| 6,500,167 B1 | 12/2002 | Webster, Jr. | |
| 6,544,262 B2 | 4/2003 | Fleischman | |
| 6,585,717 B1 * | 7/2003 | Wittenberger et al. | 604/523 |
| 6,599,288 B2 | 7/2003 | Maguire et al. | |
| 6,605,086 B2 * | 8/2003 | Hayzelden et al. | 606/41 |
| 6,605,087 B2 | 8/2003 | Swartz et al. | |
| 6,610,058 B2 * | 8/2003 | Flores | 606/41 |
| 6,645,202 B1 | 11/2003 | Pless et al. | |
| 6,689,128 B2 | 2/2004 | Sliwa et al. | |
| 6,701,931 B2 | 3/2004 | Sliwa et al. | |
| 6,702,811 B2 | 3/2004 | Stewart et al. | |
| 6,719,755 B2 | 4/2004 | Sliwa, Jr. et al. | |
| 6,743,227 B2 | 6/2004 | Seraj et al. | |
| 6,749,560 B1 * | 6/2004 | Konstorum et al. | 600/143 |
| 6,752,805 B2 | 6/2004 | Maguire et al. | |
| 6,805,128 B1 | 10/2004 | Pless et al. | |
| 6,805,129 B1 | 10/2004 | Pless et al. | |
| 6,840,936 B2 | 1/2005 | Sliwa, Jr. et al. | |
| 6,858,026 B2 | 2/2005 | Sliwa et al. | |
| 6,872,205 B2 | 3/2005 | Lesh et al. | |
| 6,942,661 B2 | 9/2005 | Swanson | |
| 6,971,394 B2 | 12/2005 | Sliwa, Jr. et al. | |
| 6,976,987 B2 * | 12/2005 | Flores | 606/41 |
| 7,025,766 B2 | 4/2006 | Whayne et al. | |
| 7,052,493 B2 | 5/2006 | Vaska et al. | |
| 8,323,241 B2 * | 12/2012 | Salahieh et al. | 604/95.04 |
| 8,323,297 B2 * | 12/2012 | Hinman et al. | 606/108 |
| 2002/0065515 A1 * | 5/2002 | Falwell et al. | 606/41 |
| 2004/0034348 A1 | 2/2004 | Rashidi | |
| 2004/0167507 A1 | 8/2004 | Nita et al. | |
| 2005/0187455 A1 | 8/2005 | Rashidi | |
| 2005/0222554 A1 | 10/2005 | Wallace et al. | |
| 2006/0064123 A1 * | 3/2006 | Bonnette et al. | 606/167 |
| 2006/0095022 A1 | 5/2006 | Moll et al. | |
| 2006/0100610 A1 | 5/2006 | Wallace et al. | |
| 2006/0184106 A1 * | 8/2006 | McDaniel et al. | 604/95.04 |

* cited by examiner

STEERABLE ABLATION DEVICE

BACKGROUND OF THE INVENTION a. Field of the Invention

The instant invention relates to ablation devices, methods of using them, and steerable devices for use in medical treatments. In particular, the invention relates to devices used in conjunction with atrial fibrillation procedures and improvements related to the introduction of devices around the heart or at epicardial surfaces.

b. Background Art

A number of surgical procedures employ the use of steerable devices, such as catheters. In an atrial fibrillation treatment for ablating cardiac tissues, an alternative to the surgical incisions of the heart is the maze procedure, where transmural ablations of the heart are made within an ablation device. Such ablations may be performed either from within the chambers of the heart (endocardial ablation) using endovascular devices (e.g., catheters) introduced through arteries or veins, or from outside the heart (epicardial ablation) using devices introduced into the chest. Various ablation techniques have been used, including cryogenic, radiofrequency (RF), laser and microwave, to create elongated transmural lesions and block electrical conduction in the atrial myocardium. An advantageous use of transmural ablation rather than surgical incisions is the ability to perform the procedure on the beating heart without the use of cardiopulmonary bypass. Maintaining the proper positioning against the wall of a beating heart can also be difficult. Visualization of endocardial anatomy and endovascular devices is often inadequate and knowing the precise position of such devices in the heart can be difficult, resulting in misplaced lesions.

Epicardial ablation devices and methods useful for creating transmural lesions for the treatment of atrial fibrillation have been described in U.S. Pat. No. 7,052,493 to Vaska et al. ("Vaska") and U.S. Pat. No. 6,971,394 to Sliwa et al. ("Sliwa"), both of which are hereby expressly incorporated by reference. Sliwa describes a method of forming a transmural lesion in a wall of the heart adjacent to the pulmonary veins by placing an ablation device through a thoracic incision and then through a pericardial penetration so that the ablation device is disposed in contact with an epicardial surface of the heart. Vaska describes an ablation device and system which may be used to wrap an ablation device around the pulmonary veins at an epicardial location.

Execution of a contiguous pulmonary vein (PV) isolation procedure can occasionally present considerable challenges to the physician. Difficulties in maneuvering the devices and passing them around anatomical structures, maintaining accurate placement on a beating heart, and avoiding unintended contact with other tissues mean that a high degree of physician skill and experience may be required in some circumstances. What are needed, therefore, are devices and methods which allow for precise introduction and placement of the ablation elements in PV isolation and linear left atrial ablations. More particularly, devices and methods which insure that ablation devices are properly placed or introduced for a PV isolation or mitral isthmus ablation procedure are desired.

BRIEF SUMMARY OF THE INVENTION

It is desirable to be able to maneuver or steer an ablation cell or device near epicardial surfaces and other areas in surgical procedures without concern for the unintended movement or reaction of the device while in the body. The invention relates to a flexible assembly for use in a region of a medical or surgical device. In preferred embodiments, the flexible region comprises a set of pull wires for controllably moving a treatment end of the device, and elements to separate the pull wires and maintain the integrity of the shaft of the flexible region in order to improve the operating aspects of the device. The devices and methods can be especially useful in ablation treatments, such as ablation at cardiac or epicardial tissues.

The present invention meets these and other objectives by providing devices, assemblies, and methods for placing and controlling the movement of medical devices. For example, some steerable devices may crimp or twist if deflected too far or deflected suddenly or forcefully. In addition, some flexible device may break if deflected too far. The invention provides a medical device, such as a catheter or shaft for introduction into the body or an assembly therefor, having improved structural properties and steerable characteristics that, in part, addresses these shortcomings in some existing devices. In particular and in one aspect, the invention provides a steerable wand or shaft-type device, or assembly therefor, for controllably introducing and/or positioning an ablation element on a cardiac or epicardial surface. However, the invention is not limited to use in cardiac procedures or with ablation treatments or devices. Instead, the invention relates more generally to deflectable or steerable medical devices that contain a flexible support region that allows a desired degree of deflection and prevents crimping, breaking, twisting or other movements that may effect the controllability of the device.

Thus, in one aspect, the invention includes an assembly for a steerable device for use in surgical or ablation therapy wherein the device typically has an elongated shaft with a flexible distal region and a generally straight proximal region. In the example of an ablating device, one or more ablation elements or cells are disposed along the distal end of the device, but which need not be part of the assembly itself. A steerable deflection area is defined within the flexible region, and it includes a first anchor member, preferably a ring-shaped or other shape to accommodate the profile associated with the shaft of the device, attached to a distal portion of the flexible distal region. The anchor member has one or more passageways for one or more pull wires extending from the proximal region and one or more actuators to the distal region. The steerable deflection region comprises a coiled or interlocking flex support member designed to permit deflection to a desired angle of deflection and maintain the integrity of the interior and exterior of the device during its use in a procedure. Typically, the proximal region of the elongated shaft contains one or more actuators to control the movement of the steerable deflection region, such that, for example, the distal region and distal end of the device move in response to actuation of the one or more pull wires.

The invention also includes methods to design and produce flexible assemblies to allow a desired range of controlled motion for a distal end of a device. For example, if the desired range of deflection of the distal end is from a straight to a 60 degree angle, the flexible support member, its structure and composition, can be selected to substantially prevent the flexible region from crimping, yielding, cracking, on its interior or exterior surfaces, and/or substantially prevent blocking or interfering with the movement of pull wires, or twisting or moving in unintended directions or degrees. Thus, the distal end comprising a treatment or diagnostic element can be steered or moved more controllably by a physician using the medical device.

A particularly preferred embodiment of the invention includes steerable ablation devices having a shaft with a flexible distal region and a generally straight proximal region. One or more ablation cells are disposed along the distal end, which has a steerable deflection degree defined be a region of the device assembly within a designed flexible region. The steerable deflection region has at least one anchor member attached to a distal portion of the flexible distal region, the anchor member having passageways for one or more pull wires extending from the proximal region to the distal region. The steerable deflection region comprises a coiled or interlocking flex support member designed to permit deflection to a desired angle of deflection or range of deflection angles, and at the same time maintain the integrity of the interior and/or exterior of the steerable deflection region to prevent unintended movement, or prevent during multiple maximum deflections and relaxations of the device cracking, breaking, crimping, or yielding in the flexible region. Thus, in particularly preferred embodiments, the interlocking flex support member can be a laser cut metal or polymer formed into a ribbed-like coil, such as those shown in the figures, which maintains the integrity of the flexible region by substantially preventing breaking, cracking, yielding, or crimping of the flexible region over the course of 10 or 20 or 50 maximum deflection and relaxation cycles of the flexible region, for example. The steerable device can have two or more pull wires for deflection of the distal end in at least two directions. In preferred embodiments, the flexible region includes a flexible separating member within the steerable deflection region, where the flexible separating member is disposed in the flexible distal region to maintain the pull wires on separate sides of the interior of the flexible distal region. As described herein, the coiled or interlocking flex support member can be comprised of one or more of a polymer, metal, nitinol, or combination of two or more of these materials. The selection of the material and shape of the coiled or interlocking support member can include pre-formed linear, curved, or curvilinear shapes, for example. The steerable device typically has one or more pull wires actuated by a handle at the proximal end of the device.

The invention also includes methods of using a steerable device of the invention, such as introducing the flexible distal region and distal end of the device into a body during a surgical treatment and moving the distal end through actuating at least one pull wire. Preferred methods include those where the surgical procedure comprises ablation of cardiac or pericardial tissue, or where the ablation comprises the use of at least one ultrasound ablation element.

The foregoing and other aspects, features, details, utilities, and advantages of the present invention will be apparent from reading the following description and claims, and from reviewing the accompanying drawings.

DETAILED DESCRIPTION OF THE INVENTION

The headings (such as "Brief Summary") used are intended only for general organization of topics within the disclosure of the invention and are not intended to limit the disclosure of the invention or any aspect of it. In particular, subject matter disclosed in the "Background Art" may include aspects of technology within the scope of the invention and thus may not constitute solely background to the invention. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment.

Figure 1:
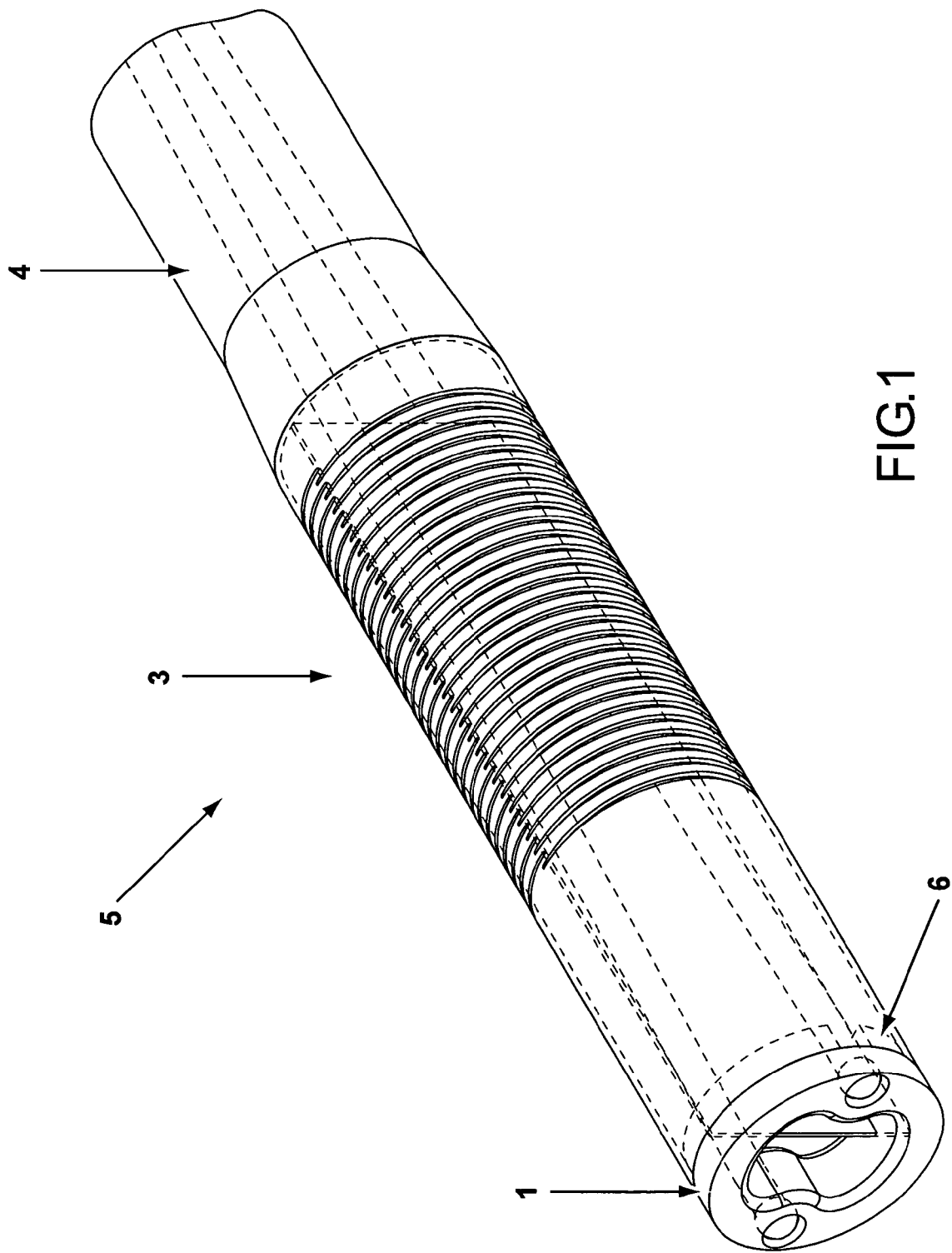
FIG. 1 depicts the flexible distal region of a device of the invention.
Figure 4:
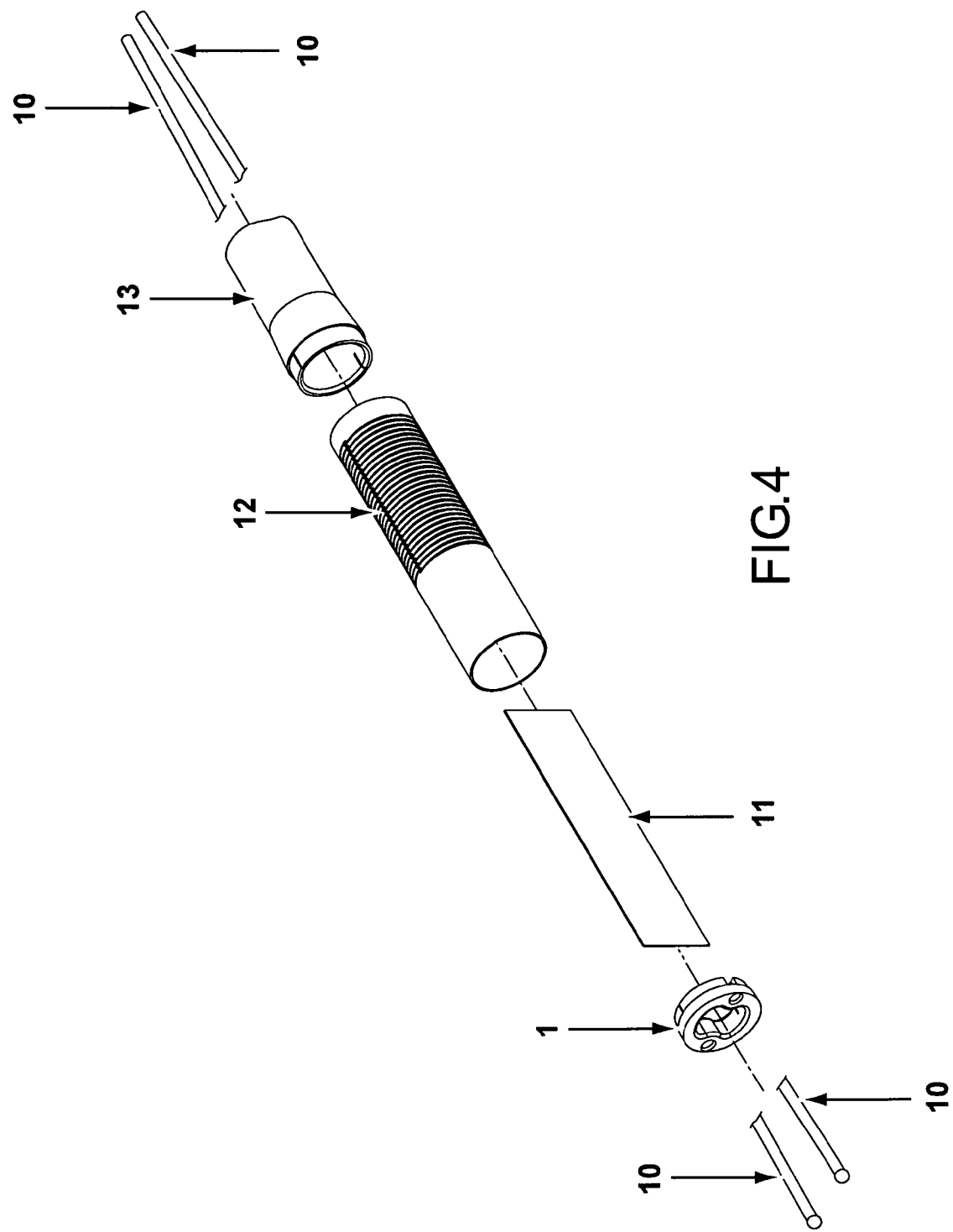
FIG. 4 depicts an exploded view of exemplary components in a flexible distal region of a device of the invention.

FIGS. 1 and 4 depict different views of a preferred embodiment of the invention comprising a flexible distal region 5 of a medical device. This assembly can be incorporated into a catheter, ablation device, or other diagnostic or treatment device and function to more controllably allow the movement of the distal end of the device in response to the physician's actions on a proximal control or actuating end or handle (not shown). Various deflectable medical devices are known and can be made available for adaptation with the present invention, including those of U.S. published patent applications 20050187455 and 20040034348, and U.S. Pat. Nos. 7,052,493 and 6,971,394, each specifically incorporated herein by reference. The device can have a pre-formed curve or curvilinear distal region or distal end for use in particular surgical procedures.

Figure 2:
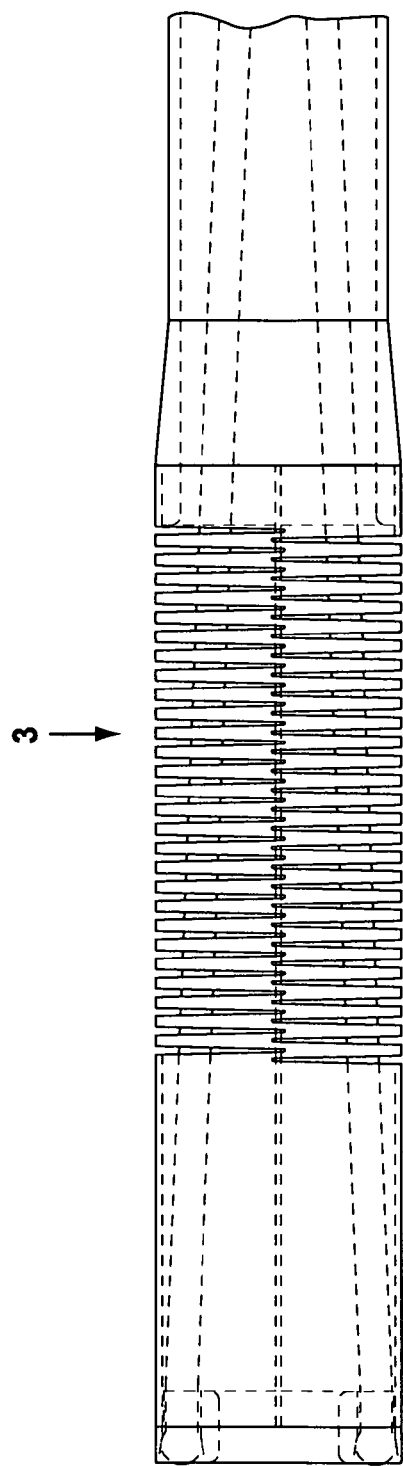
FIG. 2 depicts an embodiment of the coiled or interlocking support member of the flexible distal region.
Figure 9:
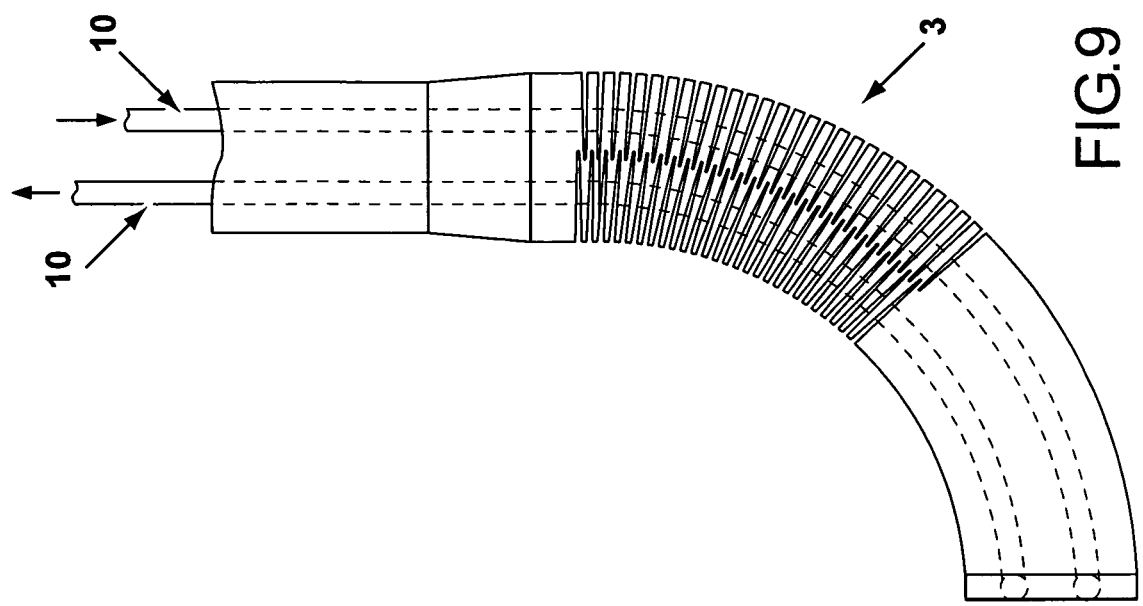
FIGS. 8 and 9 depict two additional embodiments of the coiled or interlocking support member of the flexible distal region.
Figure 8:
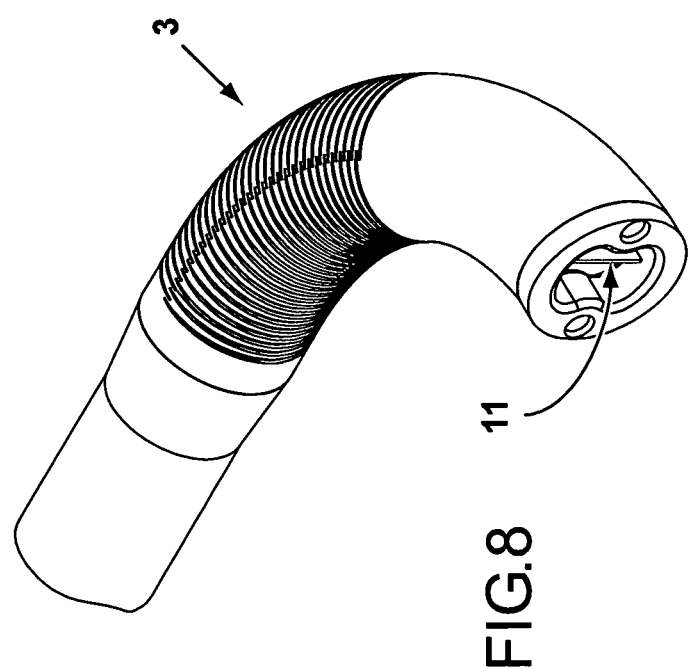
Figure 10A:
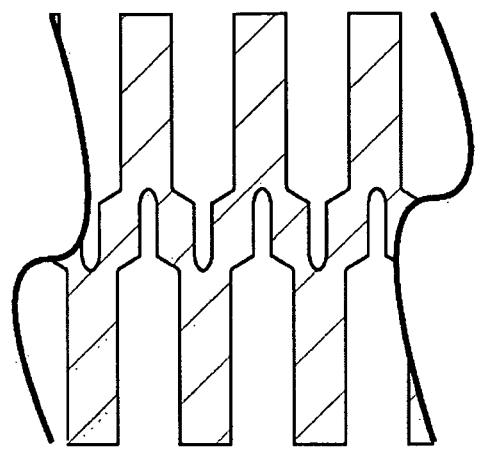
FIGS. 10 A-C schematically depict the profile shapes of some designs for laser cut embodiments of an interlocking support member.
Figure 10B:
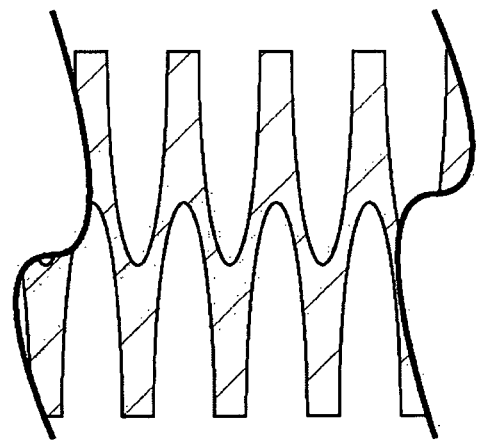
Figure 10C:
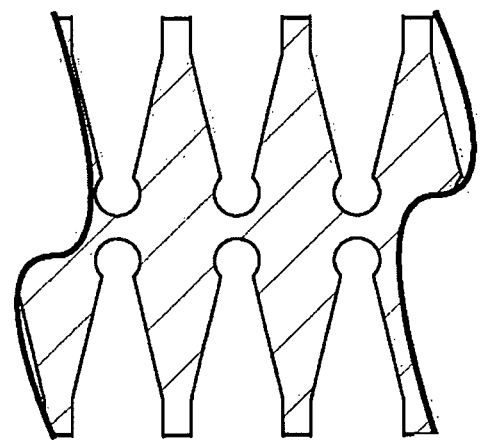

FIG. 1 shows an exemplary assembly with flexible region 5 composed in interlocking ribbed structure in a flexible support member 3, which can be any of a number of biocompatible metals, polymers, nitinol, shape-memory polymers or metals, or combinations thereof. In practice, the design of the interlocking ribbed structure should account for desired degree of deflection for a particular use. For example, interlocking pointed ends in the coiled or interlocking member 3, as shown in FIGS. 1 and 2, allow for a certain degree of movement before they become prone to crimping or separating. Similar interlocking ribbed structures with balled tips, flattened tips, or alternating tips may allow a greater degree of bending and may be desired for certain uses. FIGS. 10A-C show exemplary laser-cut designs for interlocking ribbed structures that can provide structural support and maintain the integrity of the flexible region during maximum deflection. The designs shown in FIGS. 10A-C correspond to a junction point similar to that shown in FIG. 3, where the points of each of the ribbed coils meet or come together. These structures can be formed by methods known in the art for laser cutting or other computer numerical control milling machines, for example. Alternatively, the interlocking area can be designed so that the two sides interlock when bent to a certain degree, and then can be held in place at that angle or substantially that angle until the area is bent further to release the interlocking. A number of geometrical shapes and designs can be incorporated into the interlocking area or ribbed area of the flexible support member. As shown in FIGS. 8 and 9, the assembly can include a designed orientation of the ribbed structure in relation to the direction of deflection allowed in the medical device.

Figure 3:
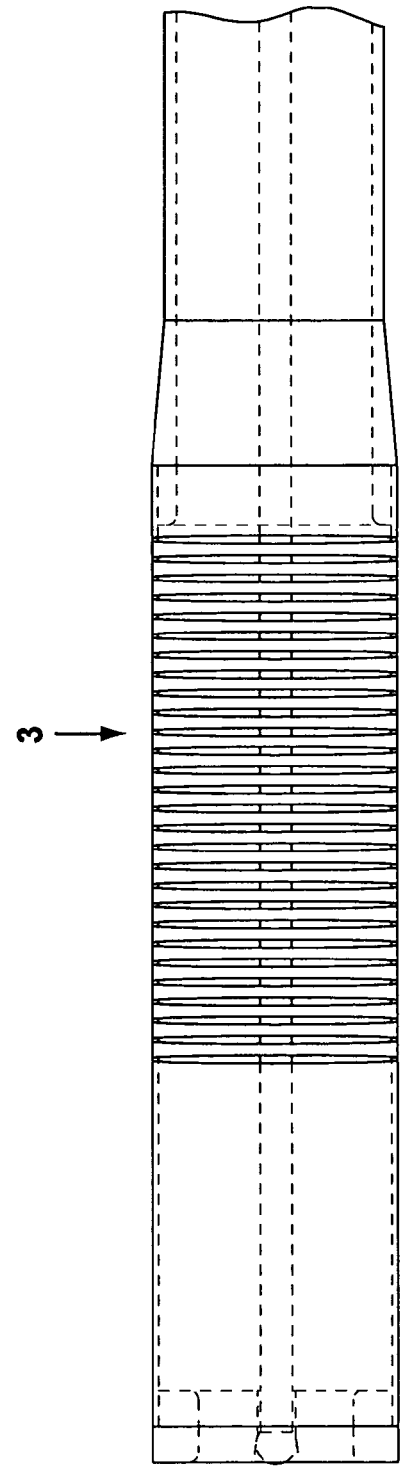
FIG. 3 depicts an alternate embodiment of the coiled or interlocking support member of the flexible distal region.

FIG. 3 depicts an alternative coiled structure for this member 3, which can similarly be made or comprised of metals, polymers, nitinol shape-memory materials. A variety of spring-like structures, braided structures, or coil structures can similarly be used to add structural integrity to the flexible distal region of a device according to the invention.

FIG. 1 further depicts the arrangement of elements in an exemplary assembly 5. Anchor member 1, here in shape of an anchor ring of the same diameter as the shaft of the device, fits into the distal end 6 of the distal flexible region of assembly. In this embodiment, a single anchor ring is used. The proximal end of the assembly 4 connects to an elongated shaft and optionally terminates in a proximal end handle and actuating elements (not shown). The exterior of the assembly and device can be coated or covered in a number of biocompatible compositions or polymers, as known in the art.

FIGS. 2 and 3 depict two of the many optional embodiments of the flexible support member 3 and its optional coiled, ribbed, or interlocking structure. The characteristics of this member can be determined by the desired flexibility, desired freedom of movement over a range of deflection angles, and/or desired strength or stress limits or Young's modulus of the material and structure selected. As noted, a number of polymeric, metal, and other material can be selected, and a preferred material is a shape-memory composition such as nitinol. Similarly and as noted above, the designs of FIGS. 10A-C can be used to produce the interlocking structure of a flex support as shown in FIG. 2 or 3, especially if laser cutting productions techniques are employed.

FIG. 4 depicts an embodiment with two pull wires 10 running through the flexible distal region assembly and the elements of the assembly. While pull wires 10 are shown to extend beyond anchor member or anchor ring 1, the pull wires can terminate at the holes or connection points in the ring in optional embodiments. A central separating member 11 fits into anchor member 1 in slits to effectively separate the interior of the flexible region so that pull wires 10 are held away from each other. The flat, plate shape of separating member 11 is one embodiment, and several other designs are possible especially when more than two pull wires are used. The separating member is typically a flexible element designed to flex and deflect with the assembly. The interlocking ribbed flex support member 12 adds structural stability and integrity to the assembly. The flex support member 12 fits onto, inside, or is integrally formed into the flexible region 3, which fits into the proximal end 1 of the shaft. The proximal end of the flexible region can also contain an anchor member or additional anchor member (not shown) to support or control movement of pull wires 10.

Figure 5:
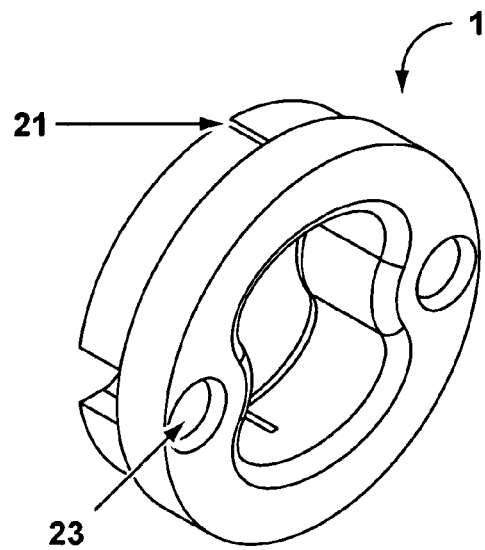
FIGS. 5 and 6 depict two views of an exemplary anchor member for use in the invention.
Figure 6:
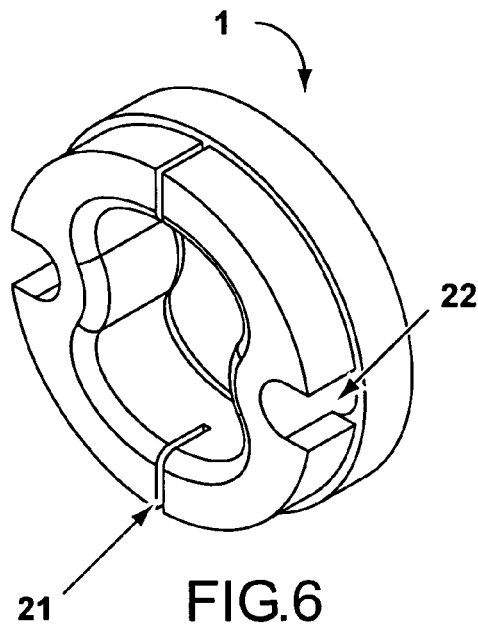

FIGS. 5 and 6 depict views of each side of the anchor member 1 and its optional features. Slots 21 are designed to hold or fix in a separating position the separating member 11, as shown in FIG. 4. Holes 23 are designed to allow pull wires to pass through and can be contoured to fit a terminating ball or other fixed point at the end of a pull wire. The differing diameters shown on the profile of anchor member 1 allow for the insertion into the flexible region of assembly. The anchor member can optionally be placed at more than one position in a flexible region assembly, such as at each of the proximal and distal end, and at the distal end, the center or intermediate point of, and the proximal end of the flexible region.

Figure 7:
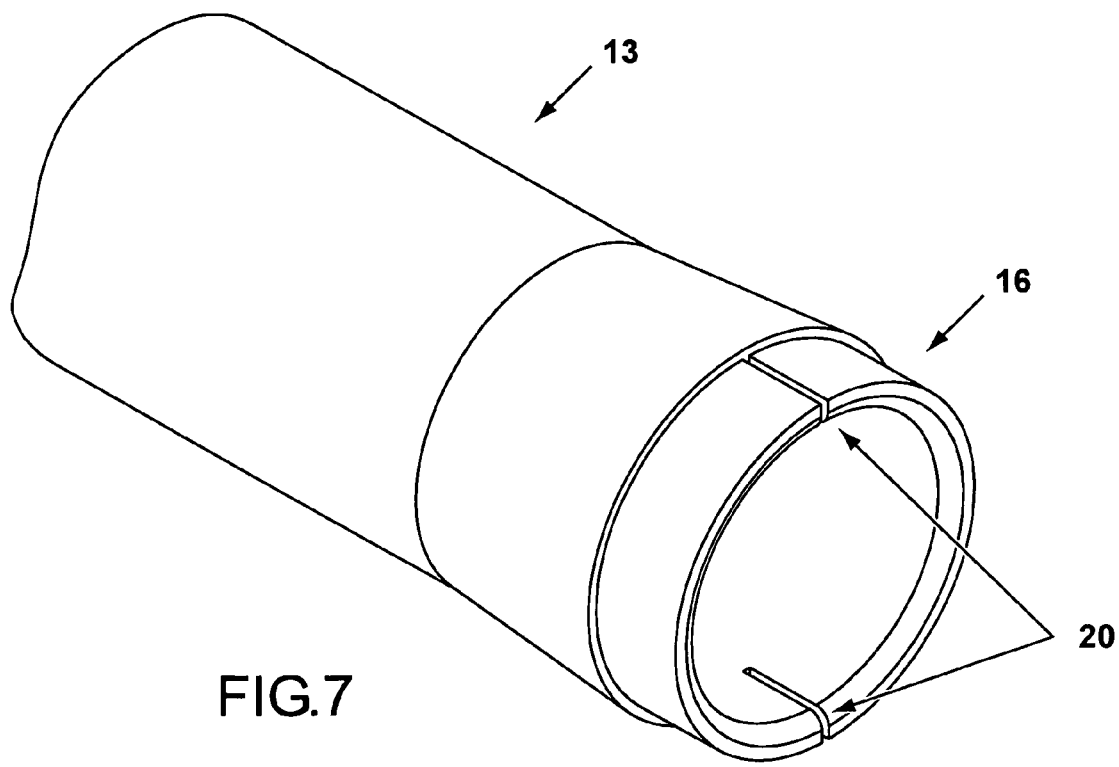
FIG. 7 depicts an exemplary connection area for the anchor member.

FIG. 7 depicts a proximal end 13 connection point for the flexible assembly, where slots 20 fix the separating member in position, and inserting diameter 16 region fits into the flexible region of assembly. FIGS. 8 and 9 depict the deflection of the flexible distal region to a desired angle.

The assemblies and devices of the invention can be used in methods to ablate cardiac or epicardial tissue, or other tissue. The flexible region assembly can be designed to allow, for example, about 90 degrees of deflection, or from about 60 to about 100 degrees of deflection, to a distal end and maintain the integrity of the flexible region and control over the movement of the ablating element at distal end. By maintaining the integrity, the interior and/or exterior walls of the flexible region do not crimp, yield, crack, or break at maximum deflection. Alternatively, the interior and/or exterior walls can withstand multiple rounds of maximum deflection and release, such as 10 rounds, 20 rounds, or 50 rounds, without substantially effecting the integrity of the interior or exterior walls by showing signs of crimping, cracking, yielding or breaking. Thus, for example, the pull wires can be actuated at a handle at the proximal end of the device to fully deflect the distal end to 90 degrees. The materials used in construction of the flexible region can be shape-memory materials that allow the flexible region to return to a desired position or move a desired angle to ablate tissue as controlled by pull wires. The deflection can be in one, two, or multiple directions with the use of a number of pull wires and connection points of the pull wires to the device or within the flexible region. The angle of deflection in each direction desired, or range of angles, can be selected from any number between, for example, 45 to 90 degrees.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, fixed, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A steerable device for use in ablation therapy, comprising
   a shaft having a flexible distal region and a generally straight proximal region;
   one or more ablation cells disposed along the distal end; and
   a steerable deflection area defined as a longitudinally-extending portion of the flexible region, the steerable deflection region having a first anchor member attached to a distal portion of the flexible distal region, the anchor member having passageways for one or more pull wires extending from the proximal region to the distal region;

wherein the steerable deflection region comprises an interlocking flex support member having a plurality of separate and distinct openings on an outer circumference of the steerable deflection region designed to permit deflection to a desired angle of deflection and maintain the integrity of the interior and exterior of the steerable deflection region, and wherein the steerable deflection region moves in response to actuation of the one or more pull wires.

2. The steerable device of claim 1, wherein the interlocking flex support member has a laser cut interlocking design that is substantially resistant to cracking, breaking or crimping after 10 or more maximum deflections.

3. The steerable device of claim 1, wherein the device has two or more pull wires for deflection of the distal end in at least two directions.

4. The steerable device of claim 2, wherein the device has two or more pull wires for deflection of the distal end in at least two directions.

5. The steerable device of claim 4, wherein the two or more pull wires are separated by a flexible separating member within the steerable deflection region.

6. The steerable device of claim 4, wherein at least two of the pull wires are disposed through holes in the first anchor member.

7. The steerable device of claim 2, wherein the interlocking flex support member is comprised of one or more of a polymer, metal, nitinol, or combination of two or more of these materials.

8. The steerable device of claim 2, wherein the interlocking flex support member has a pre-formed linear, curved, or curvilinear shape.

9. The steerable device of claim 1, wherein a second anchor member is attached to a proximal portion of the distal flexible region.

10. The steerable device of claim 9, wherein the first and second anchor members each contain one or more holes, and the one or more pull wires are disposed in at least one hole in each anchor member.

11. The steerable device of claim 10, wherein two or more pull wires each extend through a hole in each of the anchor members, and a flexible separating member is disposed in the flexible distal region to maintain the pull wires on separate sides of the interior of the flexible distal region.

12. The steerable device of claim 1, wherein the interlocking flex support member is comprised of one or more of a polymer, metal, nitinol, or a combination of two or more of these materials.

13. The steerable device of claim 1, wherein the interlocking flex support member comprises shape memory material that allows the flexible distal region to deflect in response to a pull wire and return to a pre-formed shape.

14. The steerable device of claim 1, wherein the plurality of separate and distinct openings are located with respect to each other such that, when the steerable device is deflected to a maximum angle of deflection, a first plurality of openings on an inner curve of the deflected steerable device are minimized relative to when the steerable device is undeflected and a second plurality of openings on an outer curve of the deflected steerable device are maximized relative to when the steerable device is undeflected.

15. The steerable device of claim 1, wherein the plurality of separate and distinct openings are elongate such that a plurality of ribs are formed in the outer circumference of the steerable deflection region.

16. The steerable device of claim 15, wherein the plurality of ribs are located such that, when the steerable device is deflected to a maximum angle of deflection, a plurality of ribs on an inner curve of the deflected steerable device are positioned closer together relative to when the steerable device is undeflected and a plurality of ribs on an outer curve of the deflected device are spaced further apart relative to when the steerable device is undeflected.

17. The steerable device of claim 1, wherein the one or more pull wires are actuated by a handle at the proximal end of the device.

18. A method of using a steerable device of claim 1, comprising introducing the flexible distal region and distal end of the device into a body during a surgical treatment and moving the distal end through actuating the pull wire.

19. The method of claim 18, wherein the surgical procedure comprises ablation of cardiac or pericardial tissue.

20. The method of claim 18, wherein the distal end of the device comprises at least one ultrasound ablation element.

21. The method of claim 18, wherein the device contains two or more pull wires at the flexible distal region, and the distal end of the device moves in one direction in response to the actuation of the one or more pull wires.

22. The method of claim 21, wherein the distal end moves in two or more directions in response to the actuation of the two pull wires.

23. A steerable device for use in ablation therapy, comprising a shaft having a flexible distal region and a generally straight proximal region;

one or more ablation cells disposed along the distal end; and a steerable deflection area defined within the flexible region, the steerable deflection region having a first anchor member attached to a distal portion of the flexible distal region, the anchor member having passageways for one or more pull wires extending from the proximal region to the distal region;

wherein the steerable deflection region includes at least one switchback cut that defines an interlocking flex support member designed to permit deflection to a desired angle of deflection and maintain the integrity of the interior and exterior of the steerable deflection region, and wherein the steerable deflection region moves in response to actuation of the one or more pull wires.

* * * * *